United States Patent [19]
Lamm et al.

[11] Patent Number: 5,554,737
[45] Date of Patent: Sep. 10, 1996

[54] DOUBLED ACID AZO DYES WITH A HYDROXYPYRIDONE COUPLING COMPONENT

[75] Inventors: Gunther Lamm, Haβloch; Helmut Reichelt, Neustadt; Matthias Wiesenfeldt, Mutterstadt, all of Germany

[73] Assignee: BASF Aktiengesellschaft, Ludwigshafen, Germany

[21] Appl. No.: 432,815

[22] Filed: May 2, 1995

[30] Foreign Application Priority Data

May 7, 1994 [DE] Germany .......................... 44 16 266.9

[51] Int. Cl.$^6$ ...................... C09B 31/153; C09B 33/12; D06P 1/39; D06P 1/06
[52] U.S. Cl. ...................... 534/758; 534/772; 546/261; 546/294; 546/296
[58] Field of Search ...................... 534/758, 772; 546/261, 294, 296

[56] References Cited

U.S. PATENT DOCUMENTS

| | | | |
|---|---|---|---|
| 1,880,646 | 10/1932 | Wulff | 546/294 |
| 2,406,972 | 9/1946 | Tisza et al. | 546/294 |
| 3,674,794 | 7/1972 | Mizzoni et al. | 546/294 X |
| 3,912,744 | 10/1975 | Heinrich et al. | 546/294 |
| 3,912,745 | 10/1975 | Heinrich et al. | 546/294 X |

FOREIGN PATENT DOCUMENTS

| | | | |
|---|---|---|---|
| 0313051 | 4/1989 | European Pat. Off. | 546/261 |
| 0465829 | 1/1992 | European Pat. Off. | 534/772 |
| 2150406 | 4/1973 | France | 534/758 |
| 86-01815 | 3/1986 | WIPO | 534/772 |
| WO92/14791 | 9/1992 | WIPO | 534/758 |

*Primary Examiner*—Floyd D. Higel
*Attorney, Agent, or Firm*—Oblon, Spivak, McClelland, Maier, & Neustadt, P.C.

[57] ABSTRACT

Azo dyes of the formula

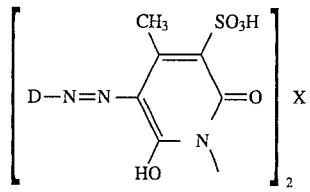

where

D is the radical of a diazo component, and

X is substituted or unsubstituted $C_2$–$C_8$-alkylene, in the form of the free acid or its salts, the use thereof for dyeing or printing natural or synthetic substrates, sulfopyridones as coupling components for these dyes, and a process for preparing them.

7 Claims, No Drawings

DOUBLED ACID AZO DYES WITH A HYDROXYPYRIDONE COUPLING COMPONENT

The present invention relates to novel azo dyes of the formula I

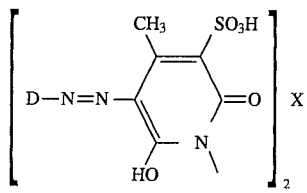

where

D is the radical of a diazo component, and

X is $C_2$–$C_8$-alkylene with or without interruption by an oxygen atom in ether function, in the form of the free acid or its salts, to the use thereof for dyeing or printing natural or synthetic substrates, to sulfopyridones as coupling components for these dyes, and to a process for preparing them.

It is an object of the present invention to provide novel azo dyes which have doubled 3-hydroxysulfonyl-4-methyl-6-hydroxypyrid-2-ones as coupling component and advantageous application properties.

We have found that this object is aclhieved by the above-defined azo dyes of the formula I.

The novel azo dyes of the formula I can be present either in the form of the free acid or else as salts.

Suitable salts are metal or ammonium salts. Metal salts include in particular the lithium, sodium or potassium salts. Ammonium salts for the purposes of the present invention are salts with subtituted or unsubstituted ammonium cations. Substituted ammonium cations include for example monoalkyl-, dialkyl-, trialkyl-, tetraalkyl- or benzyltrialkyl- ammoniumcations or cations derived from nitrogen-containing five- or six-membered saturated heterocycles, such as pyrrolidinium, piperidinium, morpholinium, piperazinium or N-alkylpiperaziniumcations or their N-monoalkyl- or N,N-dialkyl-substituted products. Alkyl for the purposes of the present invention is generally straight-chain or branched $C_1$–$C_{20}$-alkyl which may be substituted by hydroxyl groups and/or may be interrupted by from 1 to 4 oxygen atoms in ether function. Any alkyl or alkylene appearing in the abovementioned formula may be straight-chain or branched.

X is for example $CH_2$, $(CH_2)_2$, $(CH_2)_3$, $(CH_2)_4$, $(CH_2)_5$, $(CH_2)_6$, $(CH_2)_7$, $(CH_2)_8$, $CH(CH_3)CH_2$, $CH(CH_3)CH(CH_3)$, $C_2H_4OC_2H_4$, $C_3H_6OC_2H_4$, $C_3H_6OC_3H_6$, $C_4H_8OC_3H_6$ or $C_4H_8OC_4H_8$.

Of importance are azo dyes of the formula I where D is the radical of a diazo component derived from an aniline, from an aminonaphthalene or from a five-membered aromatic heterocyclic amine which contains from one to three hetero atoms selected from the group consisting of nitrogen, oxygen and sulfur in the heterocyclic ring with or without a fused-on benzene, thiophene, pyridine or pyrimidine ring.

Important azo dyes of the formula I are those where D is the radical of a diazo component derived from an aniline, from an aminonaphthalene or from a heterocyclic amine of the pyrrole, furan, thiophene, pyrazole, imidazole, oxazole, isoxazole, thiazole, isothiazole, triazole, oxadiazole, thiadiazole, benzofuran, benzothiophene, benzimidazole, benzoxazole, benzothiazole, benzisothiazole, pyridothiophene, pyrimidothiophene, thienothiophene or thienothiazole series.

Of particular importance are azo dyes of the formula I where D is the radical of a diazo component derived from an aniline or from an aminonaphthalene, anilines being especially important.

Of industrial significance are azo dyes of the formula I where D is the radical of a diazo component derived from an aminobenzophenone, from an aminoazobenzene or from an aminobenzoic acid.

D radicals conform for example to the formula

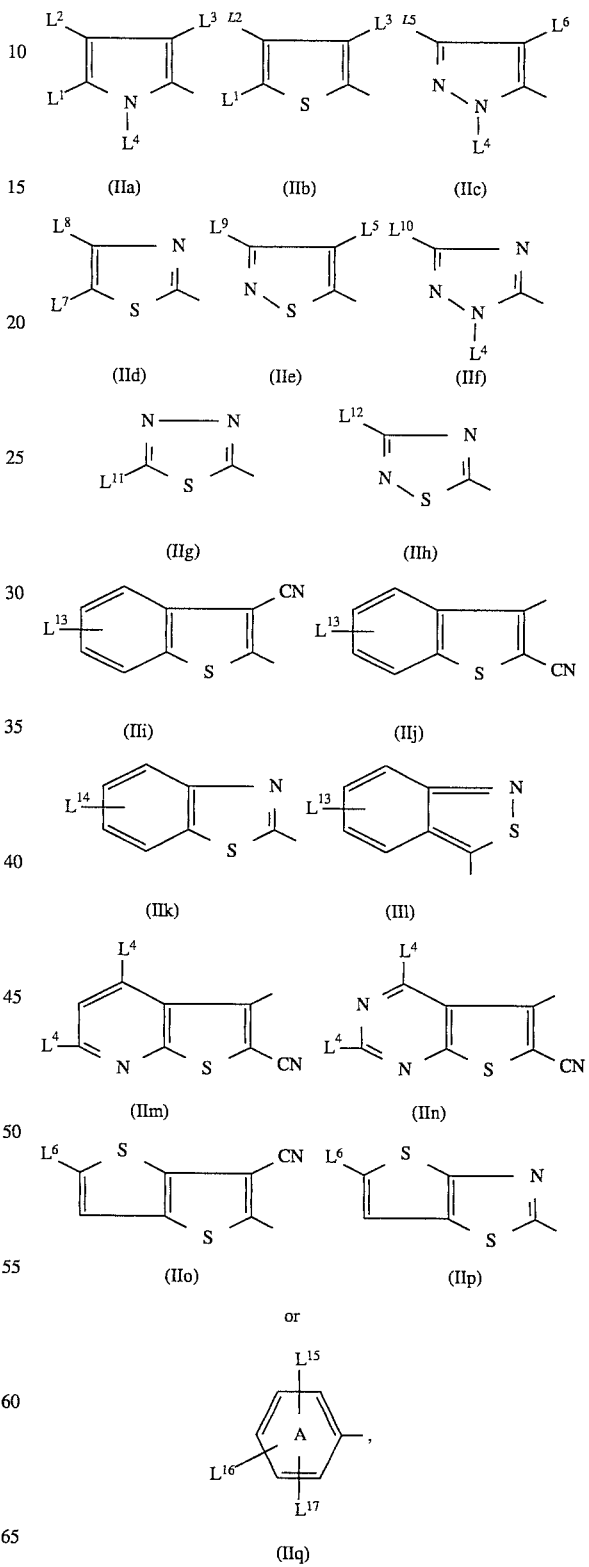

where

- $L^1$ is nitro, cyano, $C_1$–$C_6$-alkanoyl, benzoyl, $C_1$–$C_6$-alkylsulfonyl, substituted or unsubstituted phenylsulfonyl or a radical of the formula —CH═T, where T is hydroxyimino, $C_1$–$C_4$-alkoxyimino or a radical of an acidic CH compound,
- $L^2$ is hydrogen, $C_1$–$C_6$-alkyl, halogen, hydroxyl, mercapto, unsubstituted or phenyl- or $C_1$–$C_4$-alkoxy-substituted $C_1$–$C_6$-alkoxy, substituted or unsubstituted phenoxy, unsubstituted or phenyl-substituted $C_1$–$C_6$-alkylthio, substituted or unsubstituted phenylthio, $C_1$–$C_6$-alkylsulfonyl or substituted or unsubstituted phenylsulfonyl,
- $L^3$ is cyano, $C_1$–$C_4$-alkoxycarbonyl, carboxyl or nitro,
- $L^4$ is hydrogen, $C_1$–$C_6$-alkyl or phenyl,
- $L^5$ is $C_1$–$C_6$-alkyl or phenyl,
- $L^6$ is hydrogen, cyano, $C_1$–$C_4$-alkoxycarbonyl, carboxyl, $C_1$–$C_6$-alkanoyl, thiocyanato or halogen,
- $L^7$ is nitro, cyano, $C_1$–$C_6$-alkanoyl, benzoyl, $C_1$–$C_4$-alkoxycarbonyl, carboxyl, $C_1$–$C_6$-alkylsulfonyl, substituted or unsubstituted phenylsulfonyl or a radical of the formula —CH═T, where T is as defined above,
- $L^8$ is hydrogen, $C_1$–$C_6$-alkyl, cyano, halogen, unsubstituted or phenyl- or $C_1$–$C_4$-alkoxy-substituted $C_1$–$C_6$-alkoxy, unsubstituted or phenyl-substituted $C_1$–$C_6$-alkylthio, substituted or unsubstituted phenylthio, $C_1$–$C_6$-alkylsulfonyl, substituted or unsubstituted phenylsulfonyl, $C_1$–$C_4$-alkoxycarbonyl or carboxyl,
- $L^9$ is cyano, unsubstituted or phenyl-substituted $C_1$–$C_6$-alkyl, unsubstituted or phenyl-substituted $C_1$–$C_6$-alkylthio, substituted or unsubstituted phenyl, thienyl, $C_1$–$C_4$-alkylthienyl, pyridyl or $C_1$–$C_4$-alkylpyridyl,
- $L^{10}$ is phenyl or pyridyl,
- $L^{11}$ is trifluoromethyl, nitro, $C_1$–$C_6$-alkyl, phenyl, unsubstituted or phenyl-substituted $C_1$–$C_6$-alkylthio or di($C_1$–$C_6$-alkyl)amino,
- $L^{12}$ is $C_1$–$C_6$-alkyl, phenyl, 2-cyanoethylthio or 2-($C_1$–$C_4$-alkoxycarbonyl)ethylthio,
- $L^{13}$ is hydrogen, nitro or halogen,
- $L^{14}$ is hydrogen, cyano, $C_1$–$C_4$-alkoxycarbonyl, carboxyl, nitro or halogen,
- $L^{15}$ and $L^{16}$ are identical or different and each is independently of the other hydrogen, $C_1$–$C_6$-alkyl, $C_1$–$C_6$-alkoxy or halogen,
- $L^{17}$ is hydrogen, $C_1$–$C_6$-alkyl, trifluoromethyl, $C_1$–$C_6$-alkanoyl, substituted or unsubstituted benzoyl, $C_1$–$C_4$-alkoxycarbonyl, hydroxysulfonyl, substituted or unsubstituted phenylsulfonyl-oxy, mono- or di($C_1$–$C_4$-alkyl)carbamoyl, mono- or di($C_1$–$C_4$)-alkylsulfamoyl, $C_1$–$C_4$-alkanoylamino, hydroxysulfonyl- or carboxylphenyl-azo, 5-($C_1$–$C_4$-alkyl)-1,2,4-oxadiazol-3-yl or 6-hydroxysulfonyl-7-methylbenzothiazol-2-yl, and the ring A may have a fused-on benzene or hydroxysulfonylbenzene ring.

Any alkyl or alkylene appearing in the abovementioned formulae may be straight-chain or branched.

Any substituted phenyl appearing in tlhe abovementioned formulae of the azo dyes may contain as substituents for example $C_1$–$C_4$-alkyl, chlorine, bromine, nitro or $C_1$–$C_4$-alkoxy. The number of substituents in substituted phenyl is generally from 1 to 3.

The number of substituents in substituted alkyl is generally 1 or 2.

$L^2$, $L^4$, $L^5$, $L^8$, $L^9$, $L^{11}$, $L^{12}$, $L^{15}$, $L^{16}$ and $L^{17}$ are each for example methyl, ethyl, propyl, isopropyl, butyl, isobutyl, sec-butyl, pentyl, isopentyl, neopentyl, tert-pentyl, hexyl or 2-methylpentyl.

$L^9$ may also be for example benzyl or 1- or 2-phenylethyl.

$L^2$, $L^8$, $L^9$ and $L^{11}$ may each also be for example methylthio, ethylthio, propylthio, isopropyithio, butylthio, isobutylthio, pentylthio, hexylthio, benzylthio or 1- or 2-phenylethylthio.

$L^2$ and $L^8$ may each also be for example phenylthio, 2-methylphenylthio, 2-methoxyphenyithio or 2-chlorophenylthio.

$L^2$, $L^8$, $L^{15}$ and $L^{16}$ may each also be for example methoxy, ethoxy, propoxy, isopropoxy, butoxy, isobutoxy, sec-butoxy, pentyloxy, isopentyloxy, neopentyloxy, tert-pentyloxy, hexyloxy or 2-methylpentyloxy.

$L^2$, $L^8$, $L^{13}$, $L^{14}$, $L^{15}$ and $L^{16}$ may each also be for example fluorine, chlorine or bromine.

$L^7$, as well as $L^1$, $L^2$ and $L^8$, is for example methylsulfonyl, ethylsulfonyl, propylsulfonyl, isopropylsulfonyl, butylsulfonyl, isobutylsulfonyl sec-butylsulfonyl, pentylsulfonyl, isopentylsulfonyl, neopentylsulfonyl, hexylsulfonyl, phenylsulfonyl, 2-methylphenylsulfonyl, 2-methoxyphenylsulfonyl or 2-chlorophenylsulfonyl.

$L^3$, as well as $L^6$, $L^7$, $L^8$, $L^{14}$ and $L^{17}$ is for example methoxycarbonyl, ethoxycarbonyl, propoxycarbonyl, isopropoxycarbonyl, butoxycarbonyl, isobutoxycarbonyl or sec-butoxycarbonyl.

$L^2$ and $L^8$ may each also be for example 2-methoxyethoxy, 2-ethoxyethoxy, 2- or 3-methoxypropoxy, 2-or 3-ethoxypropoxy, 2- or 4-methoxybutoxy, 2- or 4-ethoxybutoxy, 5-methoxypentyloxy, 5-ethoxypentyloxy, 6-methoxyhexyloxy, 6-ethoxyhexyloxy, benzyloxy or 1- or 2-phenylethoxy.

$L^{11}$ may also be for example dimethylamino, diethylamino, dipropylamino, diisopropylamino, dibutylamino, dipentylamino, dihexylamino or N-methyl-N-ethylamino.

$L^{12}$ may also be for example 2-methoxycarbonylethylthio or 2-ethoxycarbonylethylthio.

$L^9$ may also be for example phenyl, 2-, 3- or 4-methylphenyl, 2,4-dimethylphenyl, 2-, 3- or 4-methoxyphenyl, 2-, 3- or 4-chlorophenyl, 2-, 3- or 4-methoxyphenyl, 2- or 3-methylthienyl or 2-, 3- or 4-methylpyridyl.

$L^1$ $L^6$, $L^7$ and $L^{17}$ may each also be for example formyl, acetyl, propionyl, butyryl, pentanoyl or hexanoyl.

$L^{17}$ may also be for example benzoyl, 2-, 3- or 4-methylbenzoyl, 2-, 3- or 4-ethylbenzoyl, 2-, 3- or 4-propylbenzoyl, 2-, 3- or 4-isopropylbenzoyl, 2,3-, 2,4-, 2,5-, 2,6-, 3,4- or 3,5-dimethylbenzoyl, 2-methyl-4-methoxybenzoyl, 2-, 3- or 4-methoxybenzoyl, 2-, 3- or 4-ethoxybenzoyl, phenylsulfonyloxy, 2-, 3- or 4-methylphenylsulfonyloxy, mono- or dimethylcarbamoyl, mono- or diethylcarbamoyl, mono- or dipropylcarbamoyl, mono- or diisopropylcarbamoyl, mono- or dibutylcarbamoyl, mono- or dimethylsulfamoyl, mono- or diethylsulfamoyl, mono- or dipropylsulfamoyl, mono- or diisopropylsulfamoyl, mono- or dibutylsulfamoyl, formylamino, acetylamino, propionylamino, butyrylamino, isobutyrylamino, 4-hydroxysulfonylphenylazo, 4-carboxylphenylazo, 5-methyl- 1,2,4-oxadiazol-3-yl or 5-ethyl-1,2,4-oxadiazol-3-yl.

When $L^1$ or $L^7$ is the radical —CH═T where T is derived from an acidic CH compound $H_2T$, suitable acidic CH compounds $H_2T$ include for example compounds of the formula

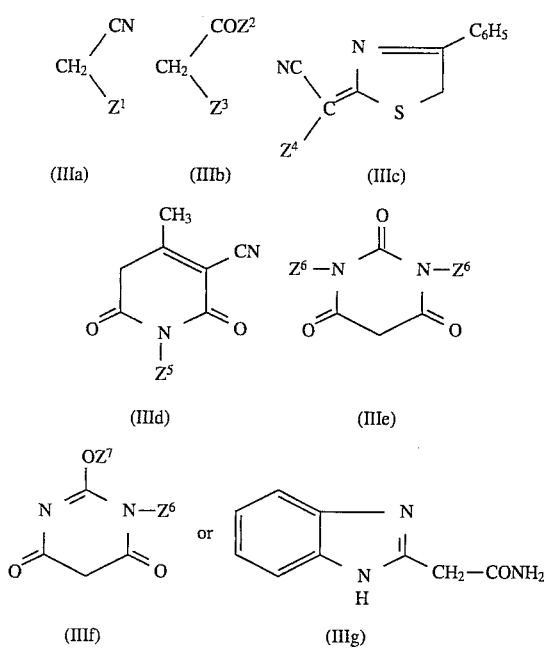

where
- $Z^1$ is cyano, nitro, $C_1$–$C_4$-alkanoyl, substituted or unsubstituted benzoyl, $C_1$–$C_4$-alkylsulfonyl, substituted or unsubstituted phenylsulfonyl, carboxyl, $C_1$–$C_4$-alkoxycarbonyl, $C_3$–$C_4$-alkenyloxycarbonyl, phenoxycarbonyl, carbamoyl, mono- or di($C_1$–$C_4$-alkyl) carbamoyl, substituted or unsubstituted phenylcarbamoyl, substituted or unsubstituted phenyl, benzothiazol-2-yl, benzimidazol-2-yl, 5-phenyl-1,3,4-thiadiazol-2-yl or 2-hydroxychinoxalin-3-yl,
- $Z^2$ is $C_1$–$C_4$-alkyl, $C_1$–$C_4$-alkoxy or $C_3$–$C_4$-alkenyloxy,
- $Z^3$ is $C_1$–$C_4$-alkoxycarbonyl, $C_3$–$C_4$-alkenyloxycarbonyl, phenylcarbamoyl or benzimidazol-2-yl,
- $Z^4$ is cyano, $C_1$–$C_4$-alkoxycarbonyl or $C_3$–$C_4$-alkenyloxycarbonyl,
- $Z^5$ is hydrogen or $C_1$–$C_6$-alkyl,
- $Z^6$ is hydrogen, $C_1$–$C_4$-Alkyl or phenyl and
- $Z^7$ is $C_1$–$C_4$-alkyl.

Attention is drawn to the radical derived from compounds of the formula IIIa, IIIb or IIIc where $Z^1$ is cyano, $C_1$–$C_4$-alkanoyl, $C_1$–$C_4$-alkoxycarbonyl or $C_3$–$C_4$-alkenyloxycarbonyl, $Z^2$ is $C_1$–$C_4$-alkyl, $C_1$–$C_4$-alkoxy or $C_3$–$C_4$-alkenyloxy, $Z^3$ is $C_1$–$C_4$-alkoxycarbonyl or $C_3$–$C_4$-alkenyloxycarbonyl and $Z^4$ is cyano.

Particular attention is drawn to the radical derived from compounds of the formula IIIa, IIIb or IIIc where $Z^1$ is cyano, $C_1$–$C_4$-alkoxycarbonyl or $C_3$–$C_4$-alkenyloxycarbonyl, $Z^2$ is $C_1$–$C_4$-alkoxy or $C_2$–$C_4$-alkenyloxy, $Z^3$ is $C_1$–$C_4$-alkoxycarbonyl or $C_3$–$C_4$-alkenyloxycarbonyl and $Z^4$ is cyano.

Preference is given to azo dyes of the formula Ia

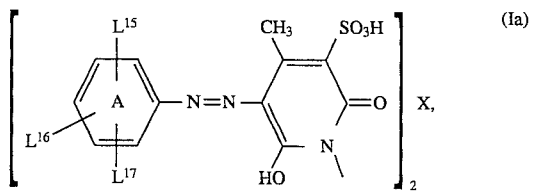

where $L^{15}$, $L^{16}$, $L^{17}$, X and the ring A are each as defined above.

Particular preference is given to azo dyes of the formula Ib

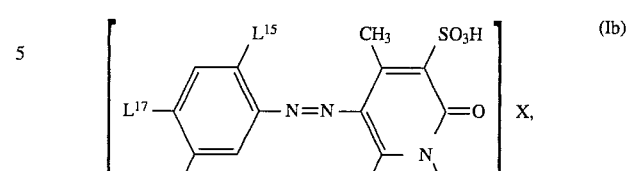

where X is as defined above, $L^{15}$ and $L^{16}$ are each hydrogen and $L^{17}$ is substituted or unsubstituted benzoyl, or $L^{15}$ and $L^{16}$ are, independently of each other, hydrogen, $C_1$–$C_4$-alkyl or $C_1$–$C_4$-alkoxy and $L^{17}$ is hydroxysulfonylphenylazo or carboxylphenylazo.

Particular preference is further given to azo dyes of the formula Ic

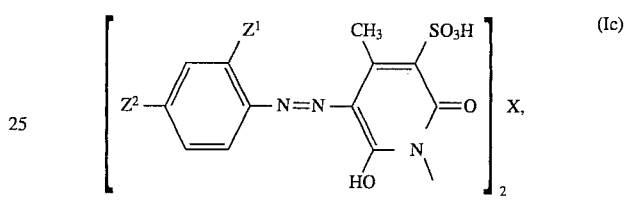

where one of $Z^1$ and $Z^2$ is hydrogen and the other is $C_1$–$C_4$-alkoxycarbonyl and X is as defined above.

The azo dyes of the formula I according to the present invention can be obtained in a conventional manner, for example by diazotizing an amine of the formula IV $$D\text{—}NH_2 \qquad (IV),$$

where D is as defined above, and coupling the resulting diazonium salt with a sulfopyridone of the formula V

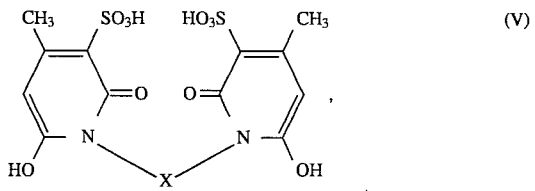

where X is as defined above.

The present invention further provides sulfopyridones of the formula V

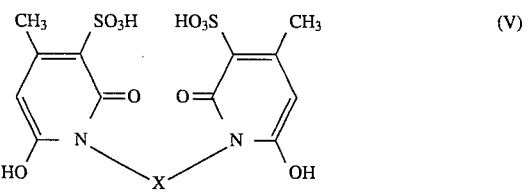

where X is $C_2$–$C_8$-alkylene with or without interruption by an oxygen atom in ether function, in the form of the free acid or its salts.

The invention also provides an advantageous process for preparing the sulfopyridones of the formula V, which comprises treating a cyanopyridone of the formula VI

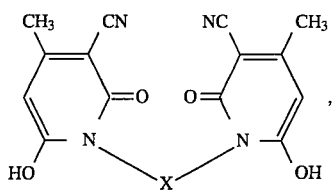

(VI)

where X is as defined above, in concentrated sulfuric acid at from 80° to 130° C.

Preferably the novel process is carried out at from 90° to 125° C.

Concentrated sulfuric acid for the purposes of the present invention is from 96 to 98 % strength by weight sulfuric acid. Generally from 2 to 2.5 parts by weight of concentrated sulfuric acid are used per part by weight of cyanopyridone VI.

The novel process is generally carried out by using concentrated sulfuric acid as initial charge and adding the cyanopyridone VI to it at room temperature. The temperature will rise and is allowed to increase to about 60°–70° C. This is followed by a period of stirring at the temperature of the present invention. The reaction will generally end after 5–8 hours, and the reaction mixture is then cooled down. It can then be added to an ice-water mixture and be neutralized. The solution thus obtained can be used directly for preparing the azo dyes of the formula I.

It can be of advantage to have small amounts of sulfur trioxide present, in which case the reaction medium is for example from 2 to 5% strength by weight oleum.

The azo dyes of the formula I according to the present invention are advantageously suitable for dyeing natural or synthetic substrates, for example wool, leather or polyamide. The dyeings obtained have good allround fastnesses.

The Examples which follow illustrate the invention.

EXAMPLE 1

163 g of the cyanopyridone of the formula

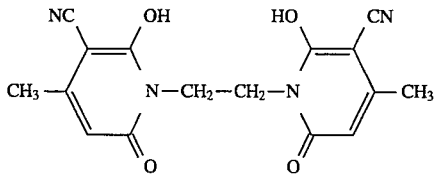

were introduced into a mixture of 40 g of oleum (24% strength by weight) and 380 g of sulfuric acid (100% strength by weight). The temperature was allowed to rise from 15° C. at the start of the addition to a maximum of 70° C. The mixture was stirred at from 70° to 80° C. for 2 h and then heated to 90° C. to split off $CO_2$. Then the reaction temperature was raised over about 4 h to 130°–135° C. in such a way that the elimination of $CO_2$ could be controlled. This was followed by stirring at from 130° to 135° C. for a further 6 h.

The melt obtained on cooling was poured with stirring onto about 1000 g of ice and 500 ml of water, and the resulting precipitation was adjusted with sodium hydroxide solution to pH 7 while cooling at <40° C. The result obtained was a clear solution (which can precipitate sodium sulfate on standing) of the sulfopyridone of the formula

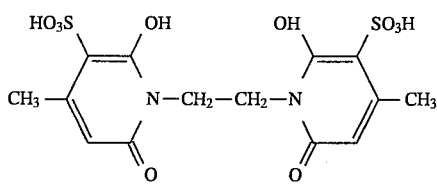

EXAMPLE 2

340 g of the cyanopyridone of the formula were introduced into a mixture of 760 g of sulfuric acid (100% strength by weight) and 80 g of oleum (24% strength by weight) and reacted as described in Example 1. About 0.97 mol was obtained of the sulfopyridone of the formula in the form of an aqueous solution.

EXAMPLE 3

30 g of 4-amino-4-methylbenzophenone hydrochloride were stirred up in 55 ml of 17% strength by weight hydrochloric acid. The mixture was then cooled down to 0° C., about 40 g of ice and at the same time 20 ml of 23% strength by weight aqueous sodium nitrite solution were added in such a way that the temperature of the diazotization batch did not rise above 10° C. The batch was subsequently stirred for a further 1 h while being cooled down with ice to 0°–5° C. After excess nitrous acid was destroyed, the pH of the resulting diazonium salt solution was raised with a little sodium acetate and sodiumhydroxide solution to 5–6 at < 0° C. Then 14.85 g of the sulfopyridone of the formula

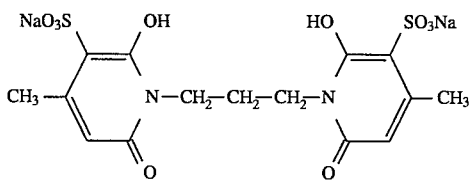

were added as an aqueous solution over 20 min while the pH was maintained within the range 4 to 7.5 by addition of sodium hydroxide solution.

The dye of the formula

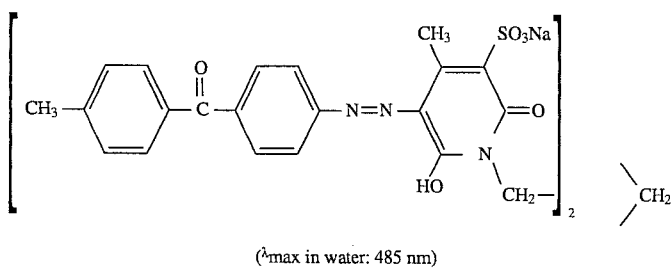

($\lambda$max in water: 485 nm)

came down as a crystalline precipitate and was isolated at pH 7 in the form of the disodium salt by salting out. Drying left 45 g of a yellow powder which gives a yellow solution in water. Dyeing 100 g of retanned chrome cattlehide leather with 0.8 g of this dye by the conventional dyeing processes gives a strong lemon yellow surface dyeing with a bright hue.

Polycaprolactam fabric is dyed by conventional dyeing processes in bright, strong, lemon yellow shades, while wool is dyed in deep neutral yellow shades.

EXAMPLE 4

10 g of ethyl 4-aminobenzoate were diazotized by the method of Example 3. Excess nitrous acid was destroyed, the pH of the diazonium salt solution was raised with a little sodium acetate and sodium hydroxide solution to 4.5–6.5 at 0° C., and then 14.85 g of the sulfopyridone mentioned in Example 2 were added in the form of an aqueous solution while the pH of the coupling batch was maintained within the above-specified range. This yielded 25 g of the dye of the formula

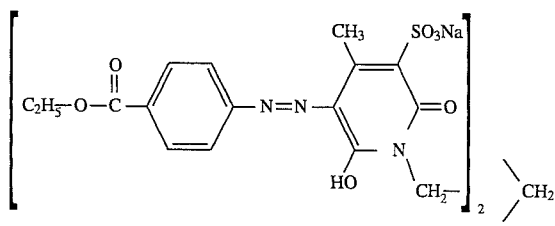

($\lambda$max in water: 406 nm)

Isolation at about pH 6.5 and drying were carried out as usual. The dye gives a yellow solution in water and dyes leather, polycaprolactam and wool in strong, lemon yellow to golden yellow hues. The dyeings have good light and wet fastnesses.

EXAMPLE 5

16.7 g of 4-aminoazobenzene-4-sulfonic acid were dissolved in 100 ml of water with sodium hydroxide solution at pH 8–9 and elevated temperature. Then 20 ml of 23% strength by weight aqueous sodium nitrite solution were added and the batch was allowed to cool down with stirring. After cooli. ng with ice down to 0° C., the batch was acidified with 20 ml of concentrated hydrochloric acid. The suspension obtained was stirred at from 0° to 5° C. for 4 h. Then excess nitrous acid was destroyed, the pH of the suspension was raised with a little sodium acetate and sodium hydroxide solution to 4.5–5.5, and an aqueous solution of 14.5 g of the sodium salt of the coupling component described in Example 1 was added similarly to Example 4. Then the reaction mixture was adjusted with sodium hydroxide solution to pH 5.5. The resulting dye was precipitated with sodium chloride, and the precipitate was isolated and dried as usual to leave 31 g of a reddish orange powder of the formula

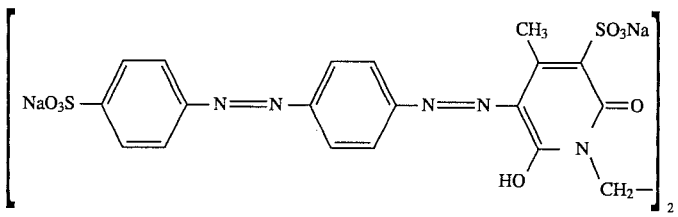

($\lambda$max in water: 444 nm)

which gives a golden yellow solution in water. The dye dyes wool, polycaprolactam and leather in a deep orange shade with good fastness properties.

The methods of Examples 1 to 5 also give the dyes described below in Tables 1 and 2.

TABLE 1

Structure:

D—N=N—[C(CH₃)=C(SO₃H)—C(=O)—N(—(CH₂)ₙ—)—C(OH)=C—]—N=N—D (bis-pyridone azo dye with central (CH₂)ₙ bridge, HO and CH₃ substituents as shown)

| Ex. No. | n | D | Hue | λ_max [nm] (in water) |
|---|---|---|---|---|
| 6 | 2 | 2-(CO₂CH₃)-phenyl | lemon yellow | 406 |
| 7 | 3 | 2-(CO₂CH₃)-phenyl | lemon yellow | |
| 8 | 4 | 2-(CO₂CH₃)-phenyl | lemon yellow | |
| 9 | 2 | 3-(5-methylisoxazol-3-yl)-phenyl | lemon yellow | 408 |
| 10 | 2 | 4-(C₂H₅NH—CO—)-phenyl | lemon yellow | |
| 11 | 2 | 4-((C₂H₅)₂N—CO—)-phenyl | lemon yellow | |
| 12 | 2 | 4-((C₂H₅)₂N—SO₂—)-phenyl | lemon yellow | |
| 13 | 2 | 3-(4-CH₃-C₆H₄—SO₃—)-phenyl | lemon yellow | |
| 14 | 2 | 4-(C₄H₉NH—SO₂—)-phenyl | lemon yellow | |

TABLE 1-continued
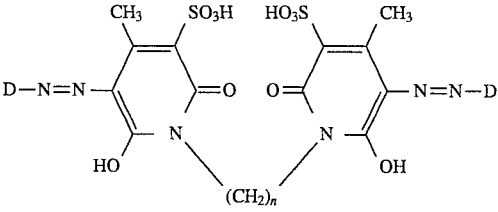
| Ex. No. | n | D | Hue | $\lambda_{max}$ [nm] (in water) |
|---|---|---|---|---|
| 15 | 3 | 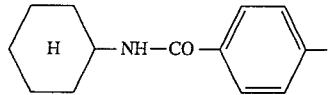 | lemon yellow | |
| 16 | 2 | 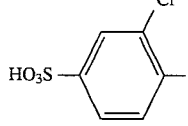 | lemon yellow | |
| 17 | 2 | 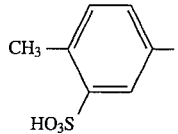 | lemon yellow | |
| 18 | 2 | 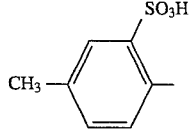 | lemon yellow | |
| 19 | 2 | 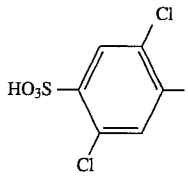 | greenish yellow | |
| 20 | 2 | 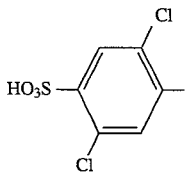 | neutral yellow | |
| 21 | 3 | (same as 20) | neutral yellow | |
| 22 | 4 | 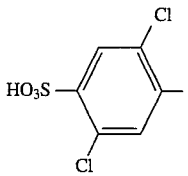 | neutral yellow | |
| 23 | 4 | 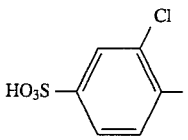 | neutral yellow | |

TABLE 1-continued
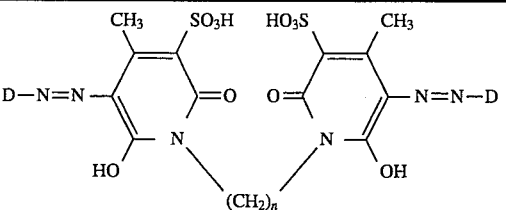
| Ex. No. | n | D | Hue | $\lambda_{max}$ [nm] (in water) |
|---|---|---|---|---|
| 24 | 2 | 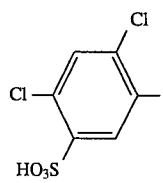 | neutral yellow | |
| 25 | 3 | 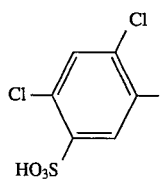 | neutral yellow | |
| 26 | 2 | 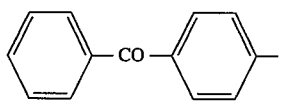 | greenish yellow | |
| 27 | 3 | 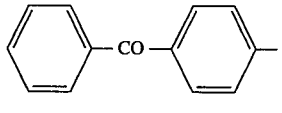 | greenish yellow | |
| 28 | 4 | 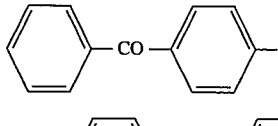 | greenish yellow | |
| 29 | 2 | 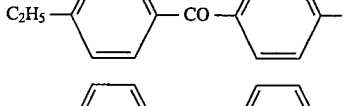 | greenish yellow | |
| 30 | 3 | 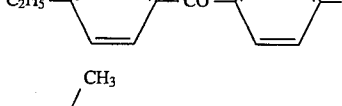 | greenish yellow | |
| 31 | 2 | 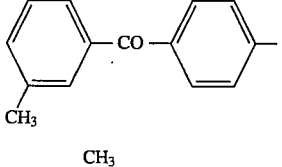 | greenish yellow | |
| 32 | 3 | 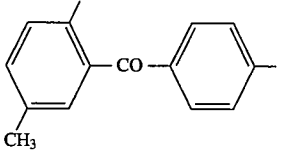 | greenish yellow | |

TABLE 1-continued
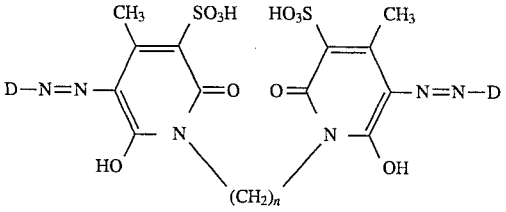
| Ex. No. | n | D | Hue | $\lambda_{max}$ [nm] (in water) |
|---|---|---|---|---|
| 33 | 2 | 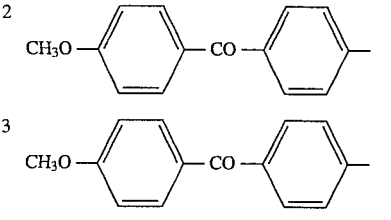 CH$_3$O—⌬—CO—⌬— | greenish yellow | |
| 34 | 3 | CH$_3$O—⌬—CO—⌬— | greenish yellow | |
| 35 | 4 | CH$_3$O—⌬—CO—⌬— | greenish yellow | |
| 36 | 2 | 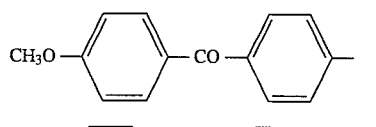 (CH$_3$)$_2$—⌬—CO—⌬— | greenish yellow | |
| 37 | 2 | C$_2$H$_5$—O—⌬—CO—⌬— | greenish yellow | |
| 38 | 2 | 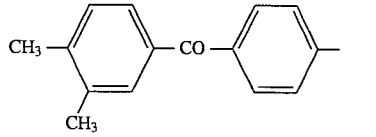 CH$_3$CONH—⌬— | neutral yellow | |
| 39 | 2 | 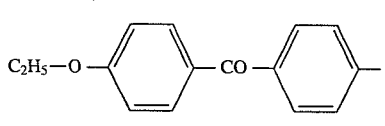 CH$_3$CONH—⌬— | neutral yellow | |
| 40 | 2 | 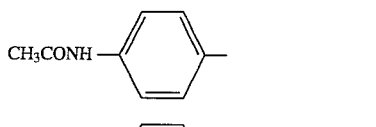 ⌬—CO$_2$C$_2$H$_5$ | greenish yellow | |
| 41 | 3 | ⌬—CO$_2$C$_2$H$_5$ | greenish yellow | |
| 42 | 4 | ⌬—CO$_2$C$_2$H$_5$ | greenish yellow | |
| 43 | 2 | 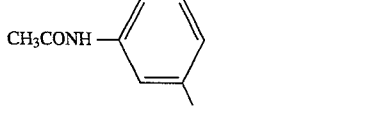 HO$_3$S—⌬—N=N—⌬— | orange | |

TABLE 1-continued

[Structure: bis-pyridone azo dye with D—N=N— groups on both sides, CH₃ and SO₃H substituents, linked by N—(CH₂)ₙ—N bridge, with HO and OH groups]

| Ex. No. | n | D | Hue | λ_max [nm] (in water) |
|---|---|---|---|---|
| 44 | 3 | HO₃S—C₆H₄—N=N—C₆H₄— | orange | |
| 45 | 2 | HO₃S—C₆H₄—N=N—(3-CH₃)C₆H₃— | orange | |
| 46 | 3 | HO₃S—C₆H₄—N=N—(3-CH₃)C₆H₃— | orange | |
| 47 | 2 | HO₃S—C₆H₄—N=N—(2,5-(CH₃)₂)C₆H₂— | orange | |
| 48 | 3 | HO₃S—C₆H₄—N=N—(2,5-(CH₃)₂)C₆H₂— | orange | |
| 49 | 2 | HO₃S—C₆H₄—N=N—(2-CH₃, 5-OCH₃)C₆H₂— | orange | |
| 50 | 2 | (3-SO₃H)C₆H₄—N=N—(2,5-(CH₃)₂)C₆H₂— | orange | |
| 51 | 3 | (3-SO₃H)C₆H₄—N=N—(2,5-(CH₃)₂)C₆H₂— | orange | |

TABLE 1-continued
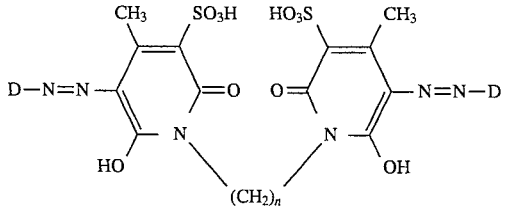
| Ex. No. | n | D | Hue | $\lambda_{max}$ [nm] (in water) |
|---|---|---|---|---|
| 52 | 2 | 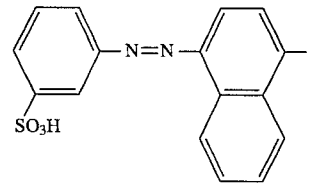 | orange | |
| 53 | 2 | 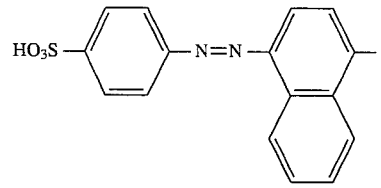 | orange | |
| 54 | 3 | 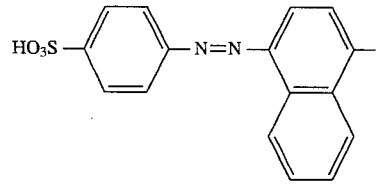 | orange | |
| 55 | 2 | 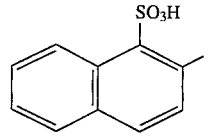 | neutral yellow | |
| 56 | 2 | 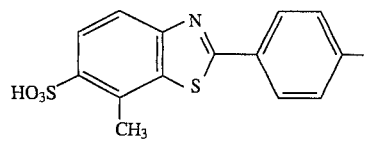 | orange | |
| 57 | 3 | 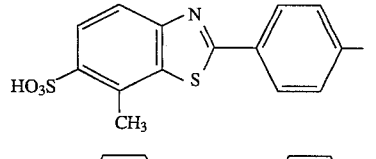 | orange | |
| 58 | 2 | 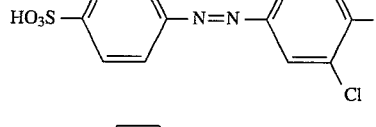 | orange | |
| 59 | 2 | 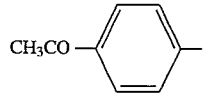 | greenish yellow | |

TABLE 1-continued
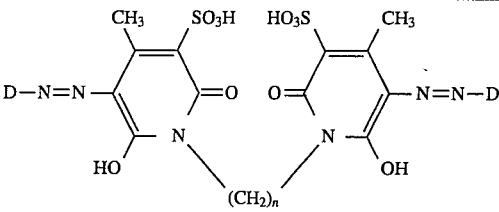
| Ex. No. | n | D | Hue | $\lambda_{max}$ [nm] (in water) |
|---|---|---|---|---|
| 60 | 2 | 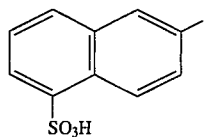 | neutral yellow | |
| 61 | 3 | 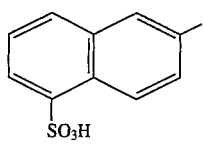 | neutral yellow | |
| 62 | 2 | 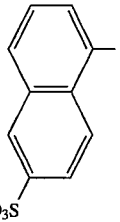 | neutral yellow | |
| 63 | 3 | 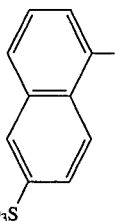 | neutral yellow | |
| 64 | 2 | 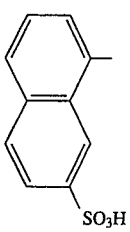 | neutral yellow | |
| 65 | 2 | 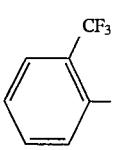 | greenish yellow | |

TABLE 2

[Structure: bis-azo pyridone dye with D—N=N— groups linked by —(CH₂)ₙ—W—(CHY)ₙ— bridge, showing CH₃, SO₃Na, HO, and N substituents on the pyridone rings]

| Ex. No. | D | n | W | Y | Hue |
|---|---|---|---|---|---|
| 66 | phenyl—CO—C₆H₄— | 1 | — | CH₃ | greenish yellow |
| 67 | CH₃—C₆H₄—CO—C₆H₄— | 1 | — | CH₃ | greenish yellow |
| 68 | 2,4-(CH₃)₂—C₆H₃—CO—C₆H₄— | 1 | — | CH₃ | greenish yellow |
| 69 | 2,5-(CH₃)₂—C₆H₃—CO—C₆H₄— | 1 | — | CH₃ | greenish yellow |
| 70 | 3,4-(CH₃)₂—C₆H₃—CO—C₆H₄— | 1 | — | CH₃ | greenish yellow |
| 71 | C₂H₅—C₆H₄—CO—C₆H₄— | 1 | — | CH₃ | greenish yellow |
| 72 | CH₃O—C₆H₄—CO—C₆H₄— | 1 | — | CH₃ | greenish yellow |
| 73 | 4-CH₃O-3-CH₃—C₆H₃—CO—C₆H₄— | 1 | — | CH₃ | greenish yellow |
| 74 | C₂H₅OCO—C₆H₄— | 1 | — | CH₃ | greenish yellow |
| 75 | HO₃S—C₆H₄—N=N—C₆H₄— | 1 | — | CH₃ | orange |

TABLE 2-continued

Structure: Bis-azo pyridone dye with general formula showing two symmetric halves connected by —(CH₂)ₙ—W—(CH(Y))ₙ— bridge between the pyridone nitrogens. Each half has CH₃, SO₃Na, =O, HO, and D—N=N— substituents.

| Ex. No. | D | n | W | Y | Hue |
|---|---|---|---|---|---|
| 76 | HO₃S—C₆H₄—N=N—(2,5-diCH₃-C₆H₃)— | 1 | — | CH₃ | orange |
| 77 | HO₃S—C₆H₄—N=N—(3-CH₃-C₆H₃)— | 1 | — | CH₃ | orange |
| 78 | (3-HO₃S-C₆H₄)—N=N—(3-CH₃-C₆H₃)— | 1 | — | CH₃ | orange |
| 79 | (3-HO₃S-C₆H₄)—N=N—(2,5-diCH₃-C₆H₃)— | 1 | — | CH₃ | orange |
| 80 | 6-HO₃S-7-CH₃-benzothiazol-2-yl-C₆H₄— | 1 | — | CH₃ | orange |
| 81 | C₂H₅O₂C—C₆H₄— | 3 | — | H | greenish yellow |
| 82 | C₂H₅O₂C—C₆H₄— | 4 | O | H | greenish yellow |
| 83 | 2-(CO₂CH₃)-C₆H₄— | 3 | — | H | greenish yellow |
| 84 | 2-(CO₂CH₃)-C₆H₄— | 4 | O | H | greenish yellow |

TABLE 2-continued

[Structure shown with D—N=N— attached to pyridone rings with CH₃, SO₃Na, HO, =O substituents, linked via N—(CH₂)ₙ—W—(CH|Y)ₙ bridge to a second pyridone bearing NaO₃S, CH₃, OH, =O and —N=N—D]

| Ex. No. | D | n | W | Y | Hue |
|---|---|---|---|---|---|
| 85 | 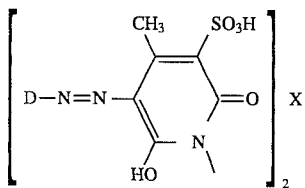 HO₃S—⟨⟩—N=N—⟨⟩— | 1 | — | H | orange |

We claim:

1. An azo dye of the formula I $$\left[ \begin{array}{c} \text{D—N=N} \underset{\underset{\text{HO}}{}}{\overset{\overset{\text{CH}_3 \quad \text{SO}_3\text{H}}{}}{\bigcirc}} =\text{O} \\ \text{N} \end{array} \right]_2 X$$

where

D is the radical of a diazo component, and

X is $C_2$–$C_8$-alkylene with or without interruption by an ether oxygen atom, in the form of the free acid or its salts.

2. The azo dye as claimed in claim 1, wherein D is the radical of an aniline, an amino-naphthalene or a five-membered aromatic heterocyclic amine which contains from one to three hetero atoms selected from the group consisting of nitrogen, oxygen and sulfur in the heterocyclic ring with or without a fused-on benzene, thiophene, pyridine or pyrimidine ring, diazo component.

3. The azo dye as claimed in claim 1, wherein D is the radical of an aniline, an amino-naphthalene, a pyrrole, a furan, a thiophene, a pyrazole, an imidazole, an oxazole, an isoxazole, a thiazole, an isothiazole, a triazole, an oxadiazole, a thiadiazole, a benzofuran, a benzothiophene, a benzimidazole, a benzoxazole, a benzothiazole, a benzisothiazole, a pyridothiophene, a pyrimidothiophene, a thienothiophene or a thienothiazole diazo component.

4. The azo dye as claimed in claim 1, wherein D is the radical of an aniline or an amino-naphthalene diazo component.

5. The azo dye as claimed in claim 1, wherein D is the radical of an aniline diazo component.

6. The azo dye as claimed in claim 1, wherein D is the radical of an aminobenzophenone, an aminoazobenzene or an aminobenzoic acid diazo component.

7. A method of dyeing or printing natural or synthetic substrates which comprises applying an azo dye of claim 1 to said substrate.

* * * * *